(12) United States Patent
Sass et al.

(10) Patent No.: US 9,395,300 B2
(45) Date of Patent: Jul. 19, 2016

(54) METHOD AND SYSTEM FOR DETERMINING THE CONCENTRATION OF SUBSTANCES IN BODY FLUIDS

(75) Inventors: Karl Sass, Kirchhain (DE); Dirk Greis, Burgwald (DE); Michael Noah, Marburg (DE); Christian Ueckermann, Marburg (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 202 days.

(21) Appl. No.: 14/233,566

(22) PCT Filed: Jul. 16, 2012

(86) PCT No.: PCT/EP2012/063864
§ 371 (c)(1),
(2), (4) Date: Jan. 17, 2014

(87) PCT Pub. No.: WO2013/010970
PCT Pub. Date: Jan. 24, 2013

(65) Prior Publication Data
US 2014/0192342 A1     Jul. 10, 2014

(30) Foreign Application Priority Data

Jul. 18, 2011   (EP) .................................. 11174320

(51) Int. Cl.
*G01N 21/59*   (2006.01)
*G01N 21/31*   (2006.01)
*G01N 33/49*   (2006.01)

(52) U.S. Cl.
CPC ............... *G01N 21/59* (2013.01); *G01N 21/31* (2013.01); *G01N 21/314* (2013.01); *G01N 33/491* (2013.01); *G01N 33/492* (2013.01); *G01N 2021/3129* (2013.01); *G01N 2021/3148* (2013.01); *G01N 2201/129* (2013.01)

(58) Field of Classification Search
None
See application file for complete search history.

(56) References Cited

U.S. PATENT DOCUMENTS

| | | | | |
|---|---|---|---|---|
| 4,001,089 A | * | 1/1977 | Stavropoulos | C12Q 1/61 435/15 |
| 4,012,196 A | * | 3/1977 | Frings | G01N 33/92 436/71 |
| 4,247,773 A | * | 1/1981 | Nexo | G01N 33/06 250/339.12 |
| 4,263,512 A | | 4/1981 | Sagusa et al. | |
| 4,554,249 A | * | 11/1985 | Kosaka | C12Q 1/26 435/10 |
| 4,839,294 A | * | 6/1989 | Almog | G01N 33/92 436/13 |
| 5,491,093 A | * | 2/1996 | Yamamoto | G01N 33/6833 436/164 |

(Continued)

FOREIGN PATENT DOCUMENTS

| | | |
|---|---|---|
| CN | 101232843 | 7/2008 |
| CN | 101542269 | 9/2009 |

(Continued)

OTHER PUBLICATIONS

European Search Report and Written Opinion of European Patent Application No. 11174320.9 dated Dec. 6, 2011.

(Continued)

*Primary Examiner* — Gordon J Stock, Jr.
(74) *Attorney, Agent, or Firm* — Dugan & Dugan, PC (57) ABSTRACT

The invention relates to a method for the spectrophotometric determination of the concentration of multiple substances, preferably bilirubin, haemoglobin and lipids, in a sample of body fluid.

15 Claims, 3 Drawing Sheets

(56) References Cited

U.S. PATENT DOCUMENTS

| | | | | |
|---|---|---|---|---|
| 5,828,445 | A | * | 10/1998 | Scharlack ............ G01N 21/274 356/300 |
| 2005/0233439 | A1 | * | 10/2005 | Everhart ................ G01N 21/31 435/287.2 |
| 2006/0063987 | A1 | * | 3/2006 | Ota .................... A61B 5/14532 600/310 |
| 2009/0009750 | A1 | | 1/2009 | Johansson |
| 2010/0174491 | A1 | | 7/2010 | Kim et al. |

FOREIGN PATENT DOCUMENTS

| | | |
|---|---|---|
| EP | 1059522 A1 | 12/2000 |
| WO | 03068060 A1 | 8/2003 |
| WO | 2006040387 A1 | 4/2006 |

OTHER PUBLICATIONS

International Search Report and Written Opinion of International Patent Application No. PCT/EP2012/063864 dated Dec. 3, 2012.

* cited by examiner

METHOD AND SYSTEM FOR DETERMINING THE CONCENTRATION OF SUBSTANCES IN BODY FLUIDS

This application is the US National Stage of International Application No. PCT/EP2012/063864, filed Jul. 16, 2012 and claims the benefit thereof. The International Application claims the benefit of European Patent Office application No. 11174320.9 filed Jul. 18, 2011. All of the applications are incorporated by reference herein in their entirety.

The present invention relates to a method and a system for determining the concentration of substances in body fluids, more particularly disruptive substances such as bilirubin, hemoglobin and lipids in blood serum and blood plasma samples.

Numerous detection and analysis methods for determining physiological parameters in body fluid samples are based on photometric measurement principles. Photometric methods allow the qualitative and quantitative detection of analytes in liquid samples.

The determination of clinically relevant parameters, for example the concentration or the activity of an analyte, is achieved in many cases by mixing in vitro an aliquot of a body fluid from a patient with one or more assay reagents, this initiating a biochemical reaction which brings about a measurable change in an optical property of the assay volume. Photometry examines and utilizes the attenuation of a luminous flux during penetration through an absorbent and/or scattering medium. Different photometric measurement methods allowing the measurement of a turbid liquid assay volume are used depending on the biochemical or biophysical reaction initiated.

Concerning this, it is possible to use turbidimetric methods in which the turbidity or the optical density of a solution or suspension is measured on the basis of the light attenuation or absorbance of a light beam passing directly through the suspension.

The intensity of the light beam decreases during penetration through a measurement cell or cuvette containing a liquid sample. The losses can be affected by interactions of the light beam with the sample located in the measurement cell, for example by absorption, diffraction, scattering and/or reflection effects. In general, diffraction and reflection effects can be disregarded or be balanced out by reference measurements, and so mainly the absorption contributes to the attenuation of the light beam.

Therefore, photometric concentration measurements are based on the absorbance or absorption being dependent, according to a law, on the concentration of the dissolved substances and on the path length of the measurement cell at a particular wavelength of the irradiated light. This relationship is described by the Beer-Lambert law:

$$E(\lambda) = -\log(I/I_0) = \epsilon(\lambda) \cdot c \cdot d \quad (1)$$

where $E(\lambda)$ is the absorbance dependent on the wavelength $\lambda$ of the light beam, I is the light intensity after penetration through the sample, I0 is the light intensity before penetration through the sample, $\epsilon(\lambda)$ is the wavelength-dependent molar extinction coefficient of an irradiated substance, c is the molar concentration of the irradiated substance, and d is the light-beam-irradiated path length of, for example, the measurement cell.

On the basis of the absorbance $E(\lambda)$ of a sample, it is possible to ascertain the concentration of a substance in a solution. To this end, it is necessary for the absorbance of at least one standard solution of known concentration to have been determined beforehand. Since absorbance is proportional to concentration, the concentration of a dissolved substance can be ascertained by means of calibration by absorbance measurements of multiple standard solutions of known concentrations.

However, the absorbance of a sample depends not only on the concentration of the substance itself to be determined, but also on the nature of the sample matrix. The absorbances of various substances behave additively in a mixture, provided the substances do not interact with one another. Body fluids, for example blood plasma or blood serum, are both complex mixtures and contain, in addition to the analyte to be determined, a multiplicity of further substances which affect the total absorption of the sample.

In individual cases, body fluid samples can, however, contain abnormally high concentrations of one or more intrinsic, i.e., endogenous, substances which can have an interfering effect in photometric detection methods when a tolerable concentration is exceeded and can result in a systematic error.

It is known that problems are caused by hemolytic, icteric and/or lipemic serum or plasma samples, which have abnormally high concentrations of hemoglobin, bilirubin and/or lipids. Abnormally high concentrations of these interfering substances can be caused by a pathological state of the patient or else by improper sample preparation or storage. If such samples are subjected to a photometric method used for determining an analytical, diagnostically relevant parameter, there is the risk of a false reading, which may possibly result in a misdiagnosis and, in the worst case, improper treatment of the patient. The preanalytical identification of hemolytic, icteric and lipemic samples is therefore of particular importance for avoiding incorrect analytical results.

There is therefore a need for methods for ascertaining the spectrometric effects of disruptive substances in body fluid samples.

EP-A1-1059522, U.S. Pat. No. 4,263,512, US 2009/0009750 A1 and US 2010/0174491 A1 describe various methods for determining bilirubin, hemoglobin and lipids in plasma or serum samples. For example, in EP-A1-1059522, there is local linear approximation of the absorbance which remains after subtraction of the absorbance owing to hemoglobin and bilirubin and which also contains in particular the absorbance caused by lipids.

However, the last-mentioned method also has the disadvantage that precisely a comparatively high lipid concentration can influence the determination of bilirubin and hemoglobin in the same sample and can thus distort the measured values.

It is therefore an object of the present invention to provide a method for spectrophotometrically determining multiple substances in a body fluid sample, which method allows, even in body fluid samples having high lipid concentrations, reliable determination of other substances, for example hemoglobin and bilirubin.

This object is achieved by the method according to the invention.

One embodiment of the present invention consists in a method for determining the concentrations of substances in a body fluid sample, comprising the steps of irradiating a light beam through a body fluid sample containing lipids and a second and, optionally, a third substance at a multiplicity of light wavelengths and of capturing a multiplicity of measured values of the absorbance of the body fluid sample at the multiplicity of wavelengths, of calculating a power-function approximation curve of the form $$E(\lambda) = p \cdot \lambda^{-q}$$

for the absorbance of the lipids (L) on the basis of a first measured value by determining the factor p at predetermined exponent q at a first wavelength at which the absorbance not caused by lipids is negligible, and of determining a first approximate value of the concentration of the second substance on the basis of a second measured value and values of the approximation curve at a second wavelength.

In an advantageous embodiment, the method additionally comprises the steps of calculating an absorbance value at a third wavelength on the basis of the first approximate value and values of the approximation curve, of ascertaining a deviation of the calculated absorbance value from a third measured value at the third wavelength, of correcting the approximation curve on the basis of the ascertained deviation, and of correcting the first approximate value on the basis of the second measured value and values of the corrected approximation curve.

In a further advantageous embodiment, the body fluid sample can additionally contain a third substance, and it is additionally possible the steps of determining a second approximate value of the concentration of a third substance on the basis of the second measured value and values of the approximation curve at a second wavelength and also of a fourth measured value and values of the approximation curve at a fourth wavelength, and of correcting the second approximate value on the basis of the second measured value, the fourth measured value and values of the corrected approximation curve, wherein the absorbance value is additionally calculated on the basis of the second approximate value.

In a preferred embodiment, the steps of calculating the absorbance value, of ascertaining the deviation, and of correcting the approximation curve, the first approximate value and the second approximate value can be iterated until the deviation is below a predetermined threshold.

Advantageously, the body fluid sample can comprise blood serum or blood plasma. In addition, it is advantageous, but not necessary, for the second substance to comprise hemoglobin and the third substance to comprise bilirubin.

In a preferred embodiment, the first wavelength is within the range between 610 nm and 650 nm, the second wavelength is within the range between 410 nm and 420 nm, the third wavelength is within the range between 360 nm and 370 nm, and the fourth wavelength is within the range between 465 nm and 475 nm.

In an advantageous embodiment, the predetermined threshold is 0.01 E.

Advantageously, the approximation curve can be corrected in such a way that the first measured value lies on the approximation curve.

In an advantageous embodiment, irradiation through the body fluid sample can be achieved using laser or light-emitting diodes and the multiplicity of measured values can be captured using a photometric sensor.

In a further embodiment, the present invention provides a system, for example an analytical instrument, for determining the concentrations of substances in a body fluid sample, comprising a measurement device designed for irradiating a light beam through a body fluid sample containing lipids and second substances at a multiplicity of light wavelengths, and for capturing a multiplicity of measured values of the absorbance of the body fluid sample at the multiplicity of wavelengths, and a calculation device designed for calculating a power-function approximation curve of the form $$E(\lambda) = p \cdot \lambda^{-q}$$

for the absorbance of the lipids (L) on the basis of a first measured value by determining the factor p at predetermined exponent q at a first wavelength at which the absorbance not caused by lipids is negligible, for determining a first approximate value of the concentration of the second substance on the basis of a second measured value and values of the approximation curve at a second wavelength, and for calculating an absorbance value at a third wavelength on the basis of the first approximate value and values of the approximation curve.

Advantageously, the calculation device is additionally designed for ascertaining a deviation of the calculated absorbance value from a third measured value at the third wavelength, for correcting the approximation curve on the basis of the ascertained deviation, and for correcting the first approximate value on the basis of the second measured value and values of the corrected approximation curve.

Advantageously, the measurement device can comprise laser or light-emitting diodes and a photometric sensor device.

In a preferred embodiment, the calculation device can be additionally designed for determining a second approximate value of the concentration of a third substance on the basis of the second measured value and values of the approximation curve at a second wavelength and also of a fourth measured value and values of the approximation curve at a fourth wavelength, and for correcting the second approximate value on the basis of the second measured value and values of the corrected approximation curve, wherein the absorbance value is additionally calculated on the basis of the second approximate value.

Further modifications and variations are apparent from the features of the dependent claims.

BRIEF DESCRIPTION OF THE FIGURES

Various embodiments and designs of the present invention will now be described in more detail with reference to the accompanying drawings.

Where meaningful, the described designs and further developments can be combined with one another in any desired combination. Other possible designs, further developments and implementations of the invention also encompass nonexplicitly stated combinations of features of the invention that have been described earlier or are described below with regard to the exemplary embodiments.

The accompanying drawings are intended to convey a further understanding of the embodiments of the invention. They illustrate embodiments and, in conjunction with the description, serve to explain principles and concepts behind the invention. Other embodiments and many of the stated advantages are revealed with reference to the drawings. The elements in the drawings are not necessarily shown true to scale in relation to one another. The same reference signs refer to identical or similarly acting components.

Body fluid samples in the context of the present invention can be all samples of biological origin which have a liquid consistency and have a multiplicity of biologically active substances in various concentrations. For example, body fluid samples can encompass blood serum, blood plasma, blood, urine, lymph, bile or similar liquids.

Photometric measured values in the context of the present invention can be measured values which can be recorded using photometric measurement devices and associated light sources, more particularly lasers, laser diodes, light-emitting diodes or the like. Measurement devices encompass, for example, CCD sensors, CMOS sensors, photosensors or similar devices suitable for capturing the intensity of a light beam in a wavelength-dependent manner.

Lipids in the context of the present application can encompass all substantially hydrophobic organic compounds, more particularly compounds occurring in the human or animal organism. Lipids in the context of the invention encompass in this regard especially fats or triglycerides or triacylglycerols which can occur in the human body.

Absorbance curves and absorbance values in the context of the present invention can be dimensionless variables which give a wavelength-dependent measure of the opacity of body fluid samples with respect to the passage of light beams in the visible, infrared and/or ultraviolet wavelength range. It may also be equally possible for absorbance values to be given with regard to unit thickness of a measurement cell or cuvette in which body fluid samples are kept during the penetration of light beams for capturing measured values relating to intensity. In this case, the absorbance values can have a dimension of [1/cm]. In any case, the indicated absorbance values of the subsequent embodiments are only of an exemplary nature and dependent on the measurement apparatus, the sample characteristics and the sample composition. Hereinafter, absorbance values will be equated in each case with absorption values, although it is clear to a person skilled in the art that although diffraction, scattering and reflection contribute to the absorbance values in this view, they are substantially negligible with respect to absorption in the wavelength range considered.

Body fluid samples can frequently contain hemoglobin, bilirubin and lipids, more particularly triacylglycerols (triglycerides). In order to determine the hemoglobin and bilirubin concentrations by means of photospectrometric methods of investigation, it is important to determine the lipid content.

Figure 1:
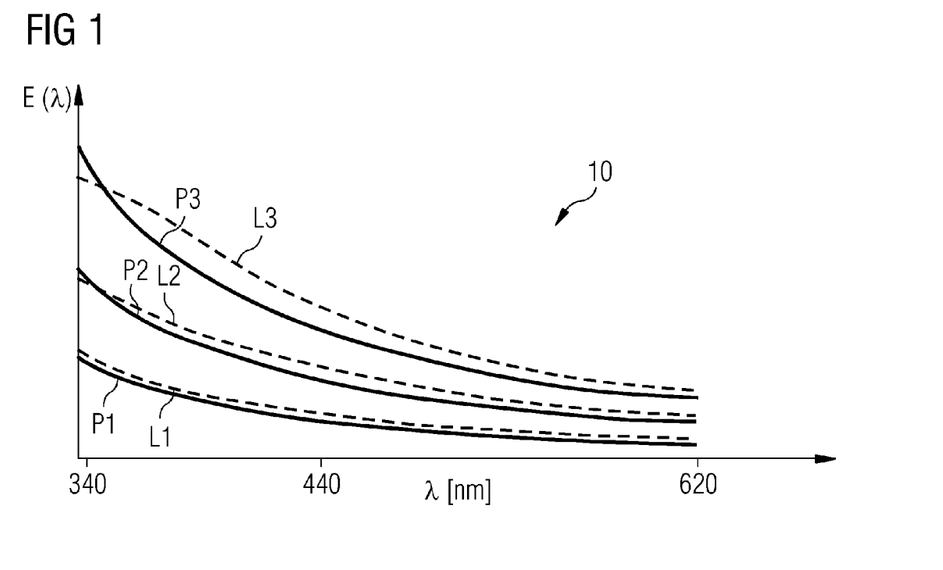
FIG. 1 shows a diagram of a graph having lipid absorbance curves according to one embodiment of the invention.

FIG. 1 shows a diagram of a graph having lipid absorbance curves in a wavelength range between about 340 nm and 620 nm. The absorbance curves L1, L2 and L3 are formed by artificially prepared lipid emulsions (Intralipid, Lipovenös®) in the lipid concentrations of 60 mg/dl, 180 mg/dl and 300 mg/dl, respectively. Firstly, it can be seen that the absorbance values overall increase with the lipid concentration. In addition, it can be seen that the absorbance for all lipid concentrations in the red visible spectral range from 600 nm to 620 nm is lower than the absorbance in the blue visible or ultraviolet spectral range. The lipid curves L1, L2 and L3 have each been approximated in FIG. 1 by a power function $$E(\lambda) = p \cdot \lambda^{-q} \quad (2)$$

to yield the approximation curves P1, P2 and P3 having in each case adapted approximation parameters p and q. The approximation parameters p and q are calculated directly from the measured absorbances and thus yield empirical values for typical orders of magnitude of the parameters p and q, which can be used in the method described below.

For the lipid curve L1 of the lowest concentration, the power curve P1 is in good agreement with the actual absorbance profile. However, for higher concentrations, the approximation curves P2 and P3 can portray the respective absorbance profiles L2 and L3 only inadequately, especially in the blue wavelength range between about 340 nm and 470 nm. Within said range, the absorbance profiles L2 and L3 form a certain absorbance plateau, this being caused by multiple scattering. However, multiple scattering occurs only in the case of the artificial lipids shown in FIG. 1. In the case of an application, however, only natural lipids occur in which there are no such multiple scatterings. Therefore, despite the deviations shown in FIG. 1, a power-function approximation allows good results in the case of an actual application, especially in comparison with, for example, local linear approximations.

Figure 2:
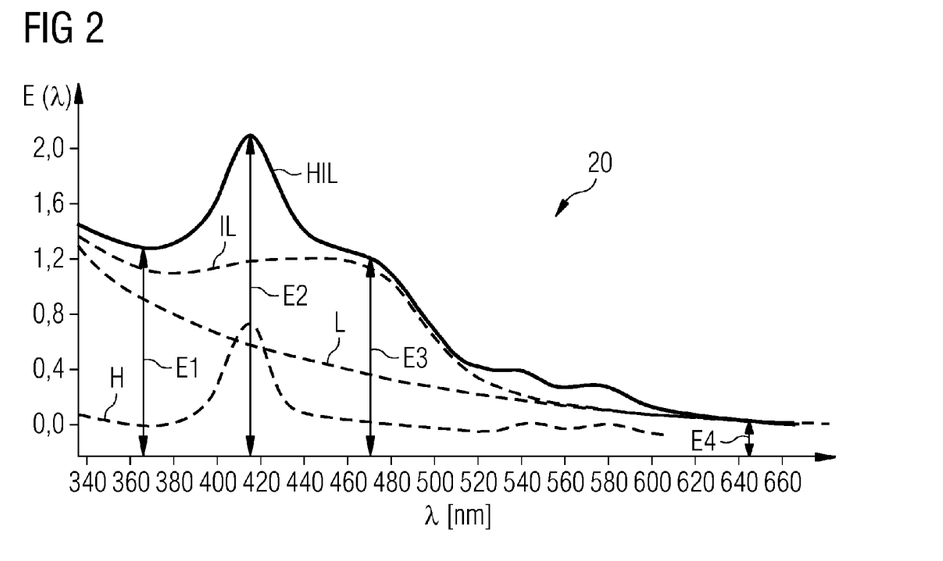
FIG. 2 shows a diagram of a graph having body fluid-sample absorbance curves according to a further embodiment of the invention.

FIG. 2 shows a diagram of a graph having body fluid-sample absorbance curves, especially of blood serum or blood plasma, within the wavelength range between 340 nm and 660 nm. Blood serum or blood plasma can comprise hemoglobin (H), bilirubin (I) and lipids (L) as emulsified substances. Determination of the concentration of these substances in the body fluid sample is therefore frequently also referred to as a HIL check.

The absorbance curve HIL displays an exemplary schematic profile for the wavelength-dependent absorbance of body fluid samples having typical concentrations of hemoglobin, bilirubin and lipids. In this regard, the absorbance curve can be split into a hemoglobin component H and a combined lipid/bilirubin component IL, the estimated absorbance curves of which are depicted in FIG. 2 as dashed curves. The pure lipid component L is likewise depicted as a dashed curve. The various absorbances overlap additively.

Within a red wavelength range between about 610 nm and 650 nm, the absorbance caused by hemoglobin and bilirubin is negligible. Thus, the absorbance is caused here largely by lipids. Therefore, with a first measurement at a first wavelength between 610 nm and 650 nm, for example at 620 nm or 645 nm, it is possible to ascertain a first measured value E4 which makes it possible, according to the Beer-Lambert law, to determine the molar lipid concentration cL [L/(mol*cm)] in a first approximation:

$$c_L = E4/\epsilon_{L4} \quad (3)$$

where $\epsilon L4$ is the molar extinction coefficient of triacylglycerols at the first wavelength.

Preferably, the concentration may also be determined using a weight-specific extinction coefficient. To this end, in the Beer-Lambert formula (formula 1), the path length d is equated to 1 mm, and the weight-specific extinction coefficient e is determined from the product of the molar extinction coefficient emol and the path length of the measurement cell d. This allows determination of the concentration of the substance in [mg/dL].

In further measurements, it is possible to capture measured values E2 and E3, which are within wavelength ranges containing absorbance maxima of hemoglobin and bilirubin, respectively. For example, the measured value E2 can be captured within a wavelength range between 410 nm and 420 nm, the maximum of hemoglobin absorbance, more particularly at about 415 nm. The measured value E3 can, for example, be captured within a wavelength range between 465 nm and 475 nm, the maximum of bilirubin absorbance, more particularly at about 470 nm. The measured value E2 is composed of absorbance components which can be attributed to hemoglobin (EH2), bilirubin (EI2) and lipids (EL2):

$$E2 = E_{H2} + E_{I2} + E_{L2} \quad (4)$$

Similarly, the measured value E3 is composed of absorbance components which can be attributed to hemoglobin (EH3), bilirubin (EI3) and lipids (EL3):

$$E3 = E_{H3} + E_{I3} + E_{L3} \quad (5)$$

Lastly, it is possible to capture a measured value E1 within a wavelength range which can be used as a control range, for example within a range between 360 nm and 370 nm, more particularly at about 365 nm. The measured value E1 is composed of absorbance components which can be attributed to hemoglobin (EH1), bilirubin (EI1) and lipids (EL1):

$$E1 = E_{H1} + E_{I1} + E_{L1} \quad (6)$$

Figure 3:
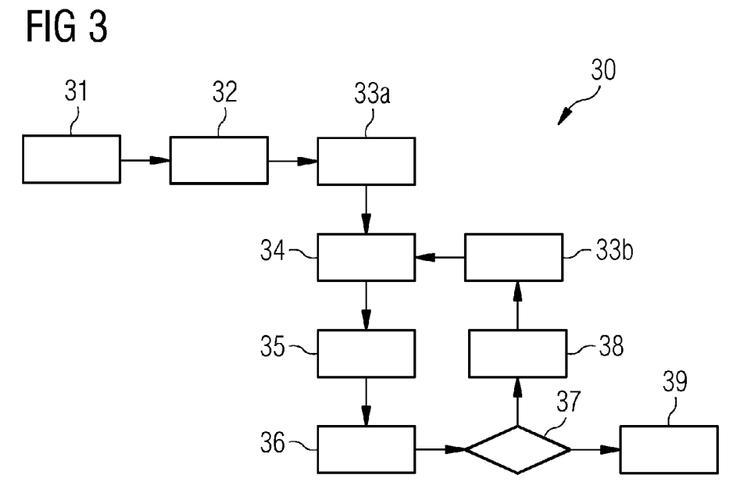
FIG. 3 shows a diagram of a method for determining the concentrations of substances in a body fluid sample according to a further embodiment of the invention.

FIG. 3 now shows a diagram of a method 30 for determining the concentrations of substances in a body fluid sample, more particularly hemoglobin, bilirubin and lipids in a blood serum or blood plasma sample.

In a first step 31, measured values E1, E2, E3 and E4, as explained in conjunction with FIG. 2, can be captured.

In a second step 32, first approximation parameters p0 and q0 for a first approximation curve L0 for the absorbance caused by lipids can be determined by means of a regression analysis. As explained in conjunction with FIG. 2, this can have the form $$E(\lambda) = p \cdot \lambda^{-q}$$

analogous to equation (2). It is self-evident that it is not yet possible to use the single measured value E4 to determine the two variables p and q in step 32. Therefore, the exponent q0 can be formed on the basis of an estimation based on the reference values shown in FIG. 1. The exponent q0 can thus be predetermined on the basis of empirical values. Since, as described in conjunction with FIG. 2, the absorbance owing to substances other than lipids can be disregarded at the first wavelength within the range from 610 to 650 nm, then, at given exponent q0 according to the equations (1), (2) and (3), it is possible to determine the coefficient p0 via the measured value E4 at the first wavelength. The thus ascertained approximation curve having the parameters p0 and q0 can reflect a first approximation for the absorbance profile of the absorbance of lipids in the sample. Concerning this, in step 33a, the respective absorbance component EL1, EL2, EL3 and EL4 (=E4) of the lipids can be calculated for all wavelengths in which further measured values have been captured in step 31.

Figure 4:
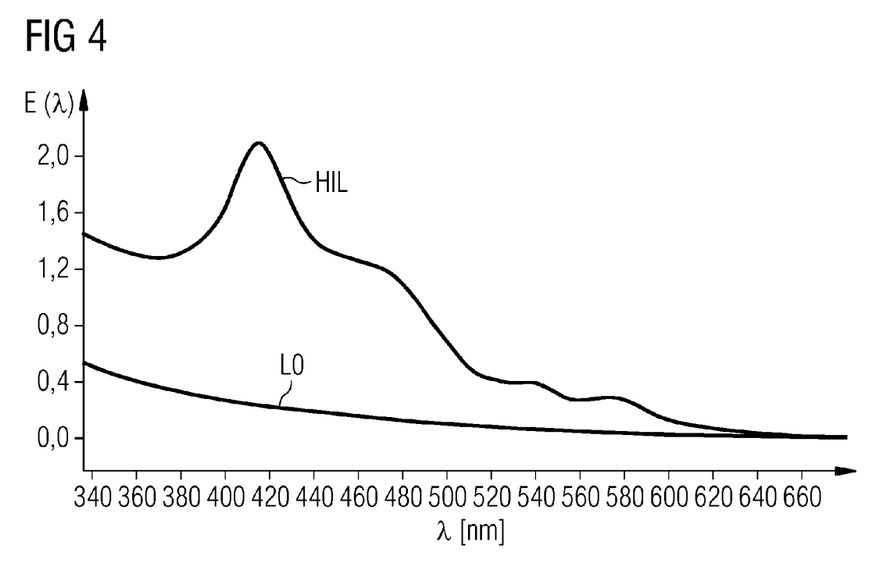
FIG. 4 shows a diagram of a graph having body fluid-sample absorbance curves according to a further embodiment of the invention.

As can be seen in FIG. 4, the result is a first approximation curve L0, which already provides a good approximation of the actual lipid absorbance. According to FIG. 1, the approximation curve L0 may be flatter, particularly in a blue or ultraviolet spectral range, than the actual absorbance profile for lipids.

In steps 34 and 35, it is then possible to determine first approximation values for the concentrations of hemoglobin (cH) and bilirubin (cI) on the basis of the measured values E2 and E3, for example at the wavelengths 415 nm and 470 nm:

$$c_I = \frac{E3 - c_H \cdot \varepsilon_{H3} - E_{L3}}{\varepsilon_{I3}} \quad (7)$$

$$c_H = \frac{E2 - c_I \cdot \varepsilon_{I2} - E_{L2}}{\varepsilon_{H2}} \quad (8)$$

where $\varepsilon H2$, $\varepsilon H3$, $\varepsilon I2$ and $\varepsilon I3$ are the respective extinction coefficients of hemoglobin (H) and bilirubin (I) at the wavelengths of the measured values E2 and E3. In this regard, the extinction coefficients can be determined beforehand by reference measurements, or from a storage device storing reference values for which calculations are retrieved.

To ascertain the two concentrations cI and cH, the system of linear equations involving the two equations (7) and (8) can be solved, yielding for the concentration of hemoglobin (H) the formula $$c_H = \frac{E3 - E_{L3} - \frac{(E2 - E_{L2}) \cdot \varepsilon_{I3}}{\varepsilon_{I2}}}{\varepsilon_{H3} - \frac{\varepsilon_{H2} \cdot \varepsilon_{I3}}{\varepsilon_{I2}}} \quad (9)$$

Here, it is possible to determine the absorbance values for the lipids EL2 and EL3 according to equation (2) using the approximation curve L0. This yields a first approximate value for the concentration cH of hemoglobin. This first approximate value for the concentration cH can then be used to determine the first approximate value for the concentration CI of bilirubin in equation (7). The result is, already, good first approximate values cH, cI and cL for the concentrations of hemoglobin, bilirubin and lipids, which were ascertained on the basis of the power function according to equation (2) and the above-described system of equations with the first approximate values for the parameters p0 and q0.

However, the approximate values can now be further improved iteratively, as will be described below. In step 36, an absorbance value EHIL can be ascertained which corresponds to an approximate value for the total absorbance at a wavelength between 360 nm and 370 nm, for example 365 nm, i.e., within a range in which a relatively high deviation of the actual lipid absorbance from the approximation curve is to be expected:

$$E_{HIL} = c_H \cdot \varepsilon_{H1} + c_I \cdot \varepsilon_{I1} + E_{L1} \quad (10)$$

The concentrations cH and cI have been determined above; the value EL1 again results from equation (2) having the parameters p0 and q0.

In step 37, a comparison between the value EHIL and the actual measured value E1 at this wavelength can then be carried out to obtain a deviation $$\Delta E = E1 - E_{HIL}$$

If the deviation $\Delta E$ is greater than a predetermined threshold, for example 10 mE, it can be determined that the ascertained approximation curve L0 for the concentrations of the lipids has not been ascertained with sufficient accuracy. In this case, correction of the approximation curve L0 can take place in step 38. To this end, the calculated absorbance value EL1, which describes the lipid absorbance component at the wavelength of 365 nm, can be corrected by a percentage of the deviation $\Delta E$. For example, half of the value of the deviation $\Delta E$ can be added to the absorbance value EL1. On the basis of the corrected absorbance value EL1, it is then possible to determine a corrected approximation curve Lk having the parameters pk and qk:

$$q_k = \frac{\ln E4 - \ln(E_{L1} + \Delta E/2)}{\ln \lambda(E4) - \ln \lambda(E1)} \quad (12)$$

$$p_k = \frac{E4}{\lambda(E4)^{-q_k}} \quad (13)$$

In this regard, equations (12) and (13) are the result of the use of the values of E4 and the corrected value $E1 + \Delta E/2$ in equation (2). This means that the approximation curve L0 can be corrected in such a way that the measured value E4, for example at the wavelength of 645 nm, continues to lie on the corrected approximation curve Lk, i.e., the measured value E4 is used as an anchor point for the approximation curve.

Figure 5:
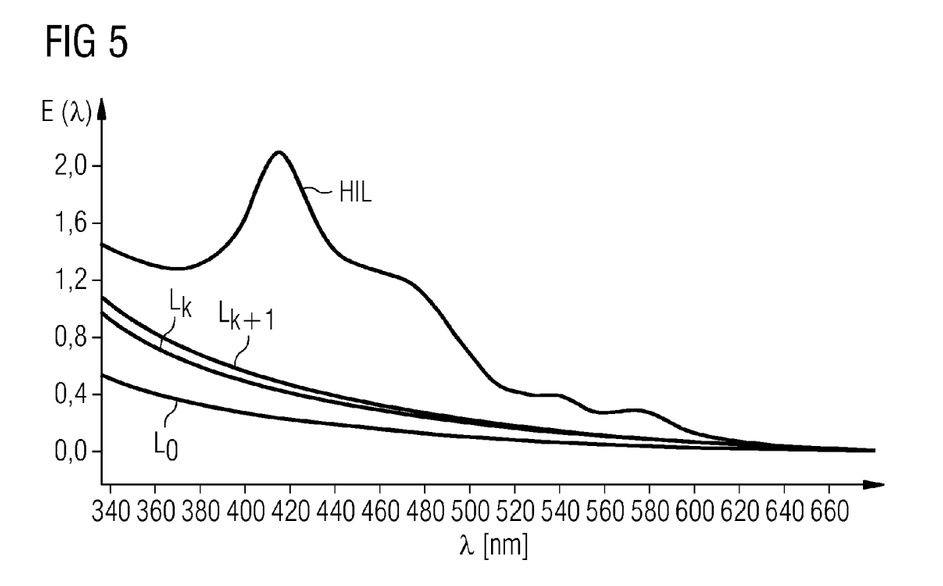
FIG. 5 shows a diagram of a graph having body fluid-sample absorbance curves according to a further embodiment of the invention.

FIG. 5 shows a diagram of the graph from FIG. 4, displaying a corrected approximation curve Lk in addition to the first approximation curve L0. The corrected approximation curve Lk has a steeper profile, particularly in the blue or ultraviolet wavelength range, than the first approximation curve L0 and is thus better suited to portraying the actual absorbance component of the lipids present in the sample.

In step 33b, it is then possible, analogous to the calculations in step 33a, to compute the respective absorbance components EL1, EL2, EL3 and EL4 (=E4) of the lipids on the basis of the corrected approximation curve Lk. The method can be iterated using steps 34, 35, 36, 37, 38 and 33b until it is determined in step 37 that the deviation falls below a predetermined threshold. In this case, the corrected approximate values for the concentrations of the substances in the body fluid sample can be outputted in step 39.

Concerning this, FIG. 5 shows by way of example an approximation curve Lk+1 which has been corrected in a subsequent iteration step and which represents, compared to the corrected approximation curve Lk, a better approximation of the actual absorbance component of the lipids present in the sample.

Figure 6:
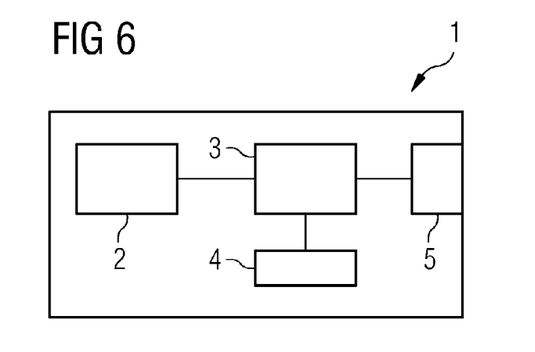
FIG. 6 shows a diagram of a system for determining the concentrations of substances in a body fluid sample according to a further embodiment of the invention.

FIG. 6 shows a diagram of a system 1 for determining the concentrations of substances in a body fluid sample, more particularly for carrying out the method 30 shown in FIG. 3. The system 1 comprises a measurement device 2, a calculation device 3, a storage device 4 and an output device 5.

The measurement device 2 can be designed for irradiating a light beam through a body fluid sample containing first and second substances at a multiplicity of light wavelengths, and for capturing a multiplicity of measured values of the absorbance of the body fluid sample at the multiplicity of wavelengths. To this end, the measurement device 2 can, for example, have light-emitting or laser diodes and corresponding photometric sensor devices.

The calculation device 3 can be designed for carrying out steps 32, 33a, 34, 35, 36, 37, 38, 33b and 39 of the method 30 in FIG. 3. More particularly, the ascertained approximate values for the concentrations of the substances can be outputted to a user of the system 1 via the output device 5.

The storage device 4 can be designed for storing predetermined values for the threshold value and/or extinction coefficients, which the calculation device 2 can retrieve if required.

The invention claimed is:

1. A method for determining concentrations of lipids and at least one further substance in a body fluid sample, comprising the steps of:
   a) irradiating light through the body fluid sample at a multiplicity of wavelengths; and
   b) capturing a multiplicity of measured values of an absorbance of the body fluid sample at the multiplicity of wavelengths;
characterized by the steps of:
   c) capturing a first measured value at a first wavelength at which an absorbance not caused by lipids is disregarded, and determining the concentration of the lipids by dividing the first measured value by an extinction coefficient specific for lipids;
   d) calculating a power-function approximation curve of the form $$E(\lambda) = p \cdot \lambda^{-q}$$

for an absorbance of the lipids based on the first measured value by determining the factor p at predetermined exponent q; and
   e) determining a first approximate value of the concentration of a second substance based on a second measured value and a value of the approximation curve at a second wavelength.

2. The method as claimed in claim 1, wherein irradiation through the body fluid sample is achieved using laser or light-emitting diodes and the multiplicity of measured values is captured using a photometric sensor.

3. The method as claimed in claim 1, comprising the steps of:
   f) calculating an absorbance value at a third wavelength based on the first approximate value and values of the approximation curve;
   g) ascertaining a deviation of the calculated absorbance value from a third measured value at the third wavelength;
   h) correcting the approximation curve based on the ascertained deviation; and
   i) determining the concentration of the second substance by correcting the first approximate value based on the second measured value and values of the corrected approximation curve.

4. The method as claimed in claim 3, wherein the approximation curve is corrected in such a way that the first measured value lies on the approximation curve.

5. The method as claimed in claim 3, wherein a third substance in the body fluid sample is additionally determined, additionally comprising the steps of:
   j) determining a second approximate value of the concentration of the third substance based on the second measured value and a value of the approximation curve at the second wavelength and also of a fourth measured value and a value of the approximation curve at a fourth wavelength; and
   k) determining the concentration of the third substance by correcting the second approximate value on the basis of the second measured value, the fourth measured value and values of the corrected approximation curve, wherein the absorbance value is additionally calculated the second approximate value.

6. The method as claimed in claim 5, wherein the first wavelength is within a range between 610 nm and 650 nm, the second wavelength is within a range between 410 nm and 420 nm, the third wavelength is within a range between 360 nm and 370 nm, and the fourth wavelength is within a range between 465 nm and 475 nm.

7. The method as claimed in claim 5, wherein the steps of calculating the absorbance value, of ascertaining the deviation, and of correcting the approximation curve, the first approximate value and the second approximate value are iterated until the deviation is below a predetermined threshold.

8. The method as claimed in claim 7, wherein the second substance comprises hemoglobin and the third substance comprises bilirubin.

9. The method as claimed in claim 7, wherein the predetermined threshold is 10 mE.

10. A system for determining concentrations of substances in a body fluid sample, comprising:
    a measurement device designed for irradiating light beams having a multiplicity of wavelengths through the body fluid sample, and for capturing a multiplicity of measured values of an absorbance of the body fluid sample at the multiplicity of wavelengths; and a calculator designed for calculating a power-function approximation curve of the form $$E(\lambda) = p \cdot \lambda^{-q}$$

for an absorbance of lipids based on a first measured value by determining the factor p at predetermined exponent q at a first wavelength at which an absorbance not caused by lipids is disregarded, and for determining a first approximate value of the concentration of a second substance based on a second measured value and a value of the approximation curve at a second wavelength.

11. The system as claimed in claim 10, wherein the calculator is designed for calculating an absorbance value at a third wavelength based on the first approximate value and values of the approximation curve, for ascertaining a deviation of the calculated absorbance value from a third measured value at the third wavelength, for correcting the approximation curve based on the ascertained deviation, and for correcting the first approximate value based on the second measured value and values of the corrected approximation curve.

12. The system as claimed in claim 11, wherein the measurement device comprises laser or light-emitting diodes and a photometric sensor device.

13. The system as claimed in claim 11, wherein the calculator is additionally designed for determining a second approximate value of the concentration of a third substance based on the second measured value and a value of the approximation curve at a second wavelength and also of a fourth measured value and a value of the approximation curve at a fourth wavelength, and for correcting the second approximate value based on the second measured value and values of the corrected approximation curve, wherein the absorbance value is additionally calculated based on the second approximate value.

14. The system as claimed in claim 13, wherein the body fluid sample comprises blood serum or blood plasma, the second substance comprises hemoglobin and the third substance comprises bilirubin.

15. The system as claimed in claim 13, wherein the first wavelength is within a range between 610 nm and 650 nm, the second wavelength is within a range between 410 nm and 420 nm, the third wavelength is within a range between 360 nm and 370 nm, and the fourth wavelength is within a range between 465 nm and 475 nm.

* * * * *